US00PP35216P2

(12) United States Plant Patent
van den Hoogen

(10) Patent No.: US PP35,216 P2
(45) Date of Patent: Jun. 13, 2023

(54) *HYPERICUM* PLANT NAMED 'ALLHYGELA'

(50) Latin Name: ***Hypericum androseamum* L.**
Varietal Denomination: Allhygela

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 32 days.

(21) Appl. No.: 17/889,206

(22) Filed: Aug. 16, 2022

(51) Int. Cl.
*A01H 5/02* (2018.01)
*A01H 6/00* (2018.01)

(52) U.S. Cl.
USPC ..... Plt./442

(58) Field of Classification Search
USPC ..... Plt./226, 442
See application file for complete search history.

*Primary Examiner* — Susan McCormick Ewoldt
(74) *Attorney, Agent, or Firm* — C. Anne Whealy

(57) ABSTRACT

A new and distinct cultivar of *Hypericum* plant named 'Allhygela', characterized by its upright plant habit; vigorous growth habit; dark green-colored leaves; freely flowering habit and high fruit density; large glossy pale yellow and light yellowish green-colored fruits; and suitability as a cut flower plant.

2 Drawing Sheets

Figure 1:
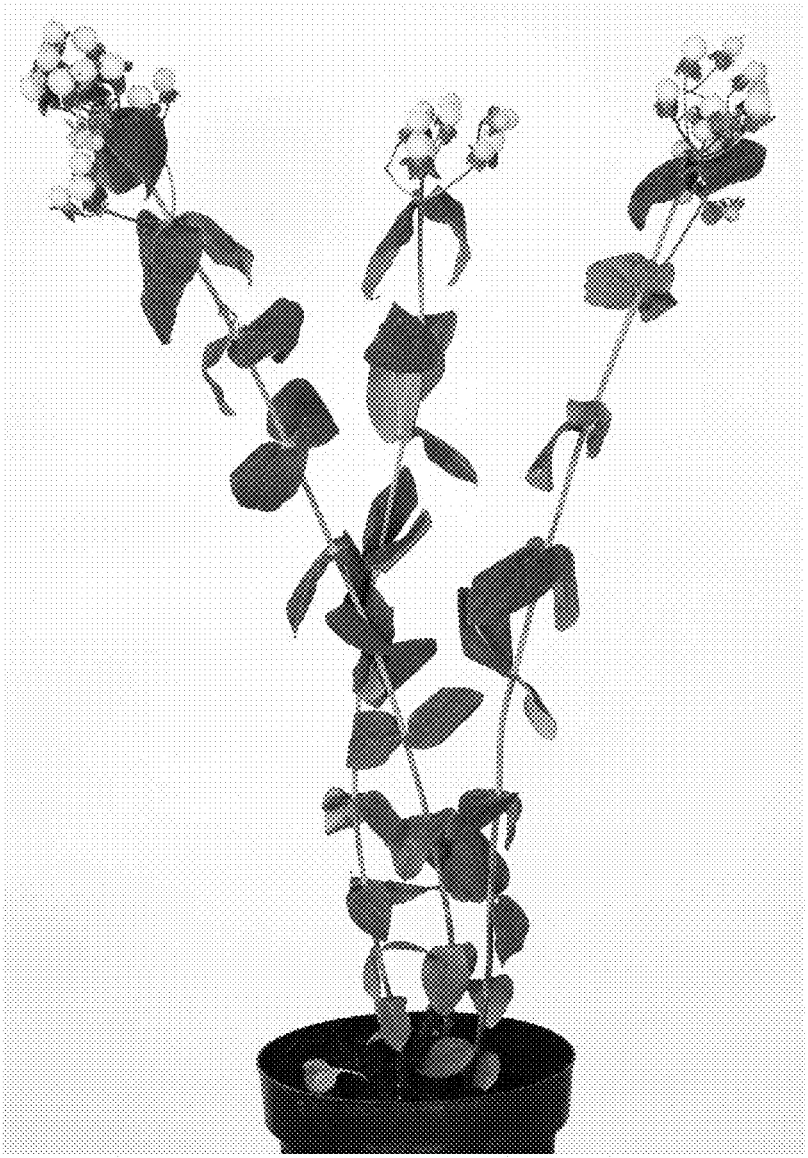

Botanical designation: *Hypericum androseamum* L.
Cultivar denomination: 'ALLHYGELA'.

STATEMENT REGARDING PRIOR DISCLOSURES BY INVENTOR/APPLICANT

An European Community Plant Breeder's Rights application for the instant plant was filed by the Assignee, Allplants Holding B.V. of Cuijk, The Netherlands on Sep. 1, 2021, application number 2021/2185. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Hypericum* plant, botanically known as *Hypericum androseamum* L., typically grown as cut flower and hereinafter referred to by the name 'Allhygela'.

The new *Hypericum* plant is a product of a planned breeding program conducted by the Inventor in Cuijk, The Netherlands. The objective of the breeding program is to create new *Hypericum* plants with numerous attractive fruits.

The new *Hypericum* plant originated from an open-pollination in September, 2012 in Cuijk, The Netherlands of a proprietary selection of *Hypericum androseamum* L. identified as code number 2-2013-59-4, not patented, as the female, or seed parent with an unknown selection of *Hypericum androseamum* L. as the male, or pollen, parent. The new

*Hypericum* plant was discovered and selected by the Inventor as a single flowering plant from within the progeny of the stated open-pollination in a controlled outdoor nursery environment in Cuijk, The Netherlands in October, 2013.

Asexual reproduction of the new *Hypericum* plant by vegetative cuttings in a controlled outdoor nursery environment in Cuijk, The Netherlands since October, 2013 has shown that the unique features of this new *Hypericum* plant are stable and reproduced true to type in successive generations.

SUMMARY OF THE INVENTION

Plants of the new *Hypericum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allhygela'. These characteristics in combination distinguish 'Allhygela' as a new and distinct *Hypericum* plant:

1. Upright plant habit.
2. Vigorous growth habit.
3. Dark green-colored leaves.
4. Freely flowering habit and high fruit density.
5. Large glossy pale yellow and light yellowish green-colored fruits.
6. Suitable as a cut flower plant.

Plants of the new *Hypericum* differ primarily from plants of the female parent selection in fruit color as plants of the new *Hypericum* have pale yellow and light yellowish green-colored fruits whereas fruits of plants of the female parent selection are light salmon pink in color.

Plants of the new *Hypericum* can be compared to plants of the *Hypericum hybrida* 'Allhy1236', disclosed in U.S. Plant Pat. No. 28,134. In side-by-side comparisons plants of the new *Hypericum* differ primarily from plants of 'Allhy1236' in the following characteristics:

1. Plants of the new *Hypericum* and 'Allhy1236' differ in fruit color as plants of the new *Hypericum* have pale yellow and light yellowish green-colored fruits whereas fruits of plants of 'Allhy1236' are white in color.
2. Fruits of plants of the new *Hypericum* are larger and more rounded in shape than fruits of plants of 'Allhy1236'.

BRIEF DESCRIPTION OF THE PHOTOGRAPHS

The accompanying colored photographs illustrate the overall appearance of the new *Hypericum* plant showing the colors as true as it is reasonably possible to obtain in colored reproductions of this type. Colors in the photographs may differ slightly from the color values cited in the detailed botanical description which accurately describe the actual colors of the new *Hypericum* plant.

The photograph on the first sheet (FIG. 1) is a side perspective view of a typical plant of 'Allhygela' when fruiting grown in a container.

Figure 2:
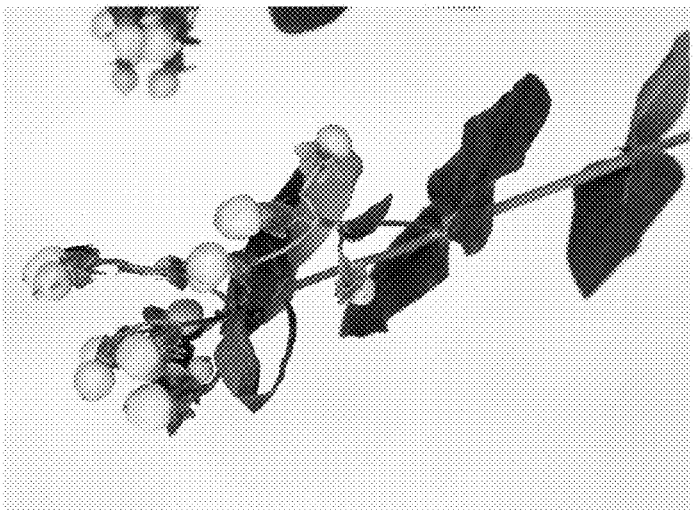

The photograph at the left of the second sheet (FIG. 2) is a close-up view of a typical fruiting stein of 'Allhygela'.

Figure 3:
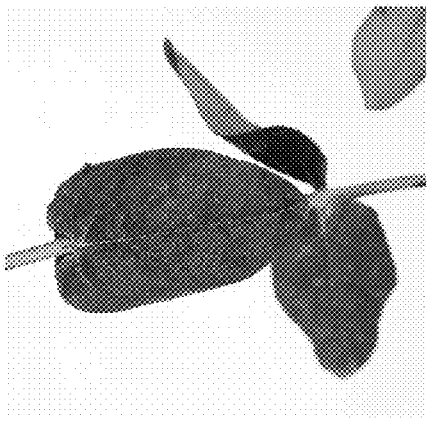

The photograph at the center of the second sheet (FIG. 3) is a close-up view of a typical stein and leaves of 'Allhygela'.

Figure 4:
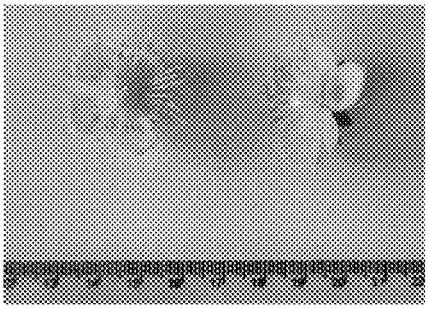

The photograph at the right of the second sheet (FIG. 4) is a close-up view of typical flowers of 'Allhygela'.

DETAILED BOTANICAL DESCRIPTION

Plants used for the aforementioned photographs and following description were grown in July in containers and ground beds in an outdoor nursery in Timau, Kenya and under cultural practices typical of commercial *Hypericum* production. During the production of the plants, day temperatures ranged from 23° C. to 28° C. and night temperatures ranged from 7° C. to 12° C. Plants were one year old when the photographs and description were taken. In the following description, color references are made to The Royal Horticultural Society Colour Chart, 2015 Edition, except where general terms of ordinary dictionary significance are used.

Botanical classification: *Hypericum androseamum* L. 'Allhygela'.

Parentage:

*Female, or seed, parent.*—Proprietary selection of *Hypericum androseamum* L. identified as code number 2-2013-59-4, not patented.

*Male, or pollen, parent.*—Unknown selection of *Hypericum androseamum* L., not patented.

Propagation:

*Type cutting.*—Vegetative cuttings.

*Time to initiate roots, summer.*—About three weeks at temperatures ranging from 12° C. to 30° C.

*Time to produce a rooted young plant, summer.*—About 24 to 32 days at temperatures ranging from 12° C. to 30° C.

*Root description.*—Fine, fleshy; typically white in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Perennial shrub; upright plant habit; overall plant shape, narrow inverted triangle; vigorous growth habit and moderate to high growth rate.

*Branching habit.*—When pinched, about three to four basal branches develop per plant.

*Plant height.*—About 63.8 cm.

*Plant width* (*spread*).—About 35.2 cm.

*Lateral branch description.*—Length: About 52.8 cm. Diameter: About 3 mm Internode length: About 5.9 cm. Strength: Moderately strong to strong. Texture and luster: Smooth, glabrous; slightly glossy. Color, developing: Close to 147D, mottled and blushed with close to N199D. Color, fully developed: Close to 200A to 200C.

Leaf description:

*Arrangement.*—Opposite, simple; sessile; about 18 leaves (nine pairs) develop per lateral branch.

*Length.*—About 6.6 cm.

*Width.*—About 4.5 cm.

*Shape.*—Ovate.

*Apex.*—Mostly obtuse.

*Base.*—Truncate to cordate.

*Margin.*—Entire.

*Texture and luster, upper surface.*—Smooth, glabrous; slightly glossy.

*Texture and luster, lower surface.*—Slightly rugose, glabrous; matte.

*Venation pattern.*—Pinnate.

*Color.*—Developing leaves, upper surface: Close to 144A. Developing leaves, lower surface: Close to a blend of 143C and 144A. Fully expanded leaves, upper surface: Close to a blend of NN137A and 147A; venation, close to 145A. Fully expanded leaves, lower surface: Close to 147B; venation, close to 152D.

Flower description:

*Flower type, arrangement and flowering habit.*—Single rotate flowers arranged in terminal and axillary compound cymes; freely flowering habit with about eleven flowers per cyme and about 19 flowers per lateral branch; flowers face mostly upright.

*Fragrance.*—None detected.

*Natural flowering season.*—Plants flower continuously June to early September in The Netherlands; plants begin flowering about ten months after planting.

*Flower longevity.*—Flowers last about three days on the plant; flowers not persistent.

*Fruit longevity* (*postproduction*).—About 30 days.

*Flower buds.*—Length: About 5 mm. Diameter: About 5 mm. Shape: Broadly elliptic. Color: Close to 7B.

*Inflorescence height.*—About 6 cm.

*Inflorescence diameter.*—About 7.9 cm.

*Flower diameter.*—About 2 cm.

*Flower depth* (*height*).—About 1.8 cm.

*Petals.*—Quantity and arrangement: Five in a single whorl. Length: About 1 cm. Width: About 9.5 mm. Shape: Broadly elliptic, concave; horizontal to moderately reflexed. Apex: Acute, unequal. Base: Attenuate. Margin: Entire. Texture and luster, upper surface: Smooth, glabrous; matte. Texture and luster, lower surface: Smooth, glabrous; moderately glossy. Color: When opening and fully opened, upper surface: Close to 13A; color does not change with subsequent development. When opening and fully opened, lower surface: Close to 14B; color does not change with subsequent development.

*Sepals.*—Quantity and arrangement: Five in a single whorl. Length: About 8.5 mm. Width: About 7 mm. Shape: Ovate to broadly ovate; slightly to strongly reflexed. Apex: Obtuse to broadly and bluntly acute. Base: Broadly cuneate. Margin: Entire. Texture and luster, upper surface: Smooth, glabrous; slightly glossy. Texture and luster, lower surface: Smooth, glabrous; matte. Color: When opening, upper surface: Close to 143A. When opening, lower surface: Close to 144B. Fully opened, upper surface: Close to 137A. Fully opened, lower surface: Close to 147B.

*Peduncles.*—Length: About 3.3 cm. Diameter: About 1.5 mm. Texture: Smooth, glabrous. Strength: Moderately strong. Aspect: Main peduncles, erect; lateral peduncles, about 55° from main peduncles axis. Color: Close to 144A.

*Pedicels.*—Length: About 1.6 cm. Diameter: About 1.5 mm. Texture: Smooth, glabrous. Strength: Moderately strong. Aspect: Main pedicels, erect; lateral pedicels, about 60° from main peduncle axis. Color: Close to 144A.

*Reproductive organs.*—Stamens: Quantity per flower: About 100. Filament length: About 1 cm. Filament color: Close to 12B. Anther length: About 0.5 mm. Anther shape: Broadly oval; dorsifixed. Anther color: Close to 16C. Pollen amount: Scarce. Pollen color: Close to 11A. Pistils: Quantity per flower: Single pistil with three stigmas. Pistil length: About 3.5 mm. Stigma shape: Club-shaped. Stigma color: Close to 145C. Style length: About 3.25 mm. Style color: Close to 151D. Ovary color: Close to 151D.

*Fruits.*—Quantity per lateral branch: About 19. Length: About 1.3 cm. Diameter: About 1.4 cm. Shape: Roughly spherical. Texture and luster: Smooth, glabrous; glossy. Color: Close to 160B to 160C; proximally, fading to close to 150D.

*Seeds.*—Quantity per fruit: About 100. Length: About 0.9 mm. Diameter: About 0.5 mm. Color: Close to 200A.

Pathogen & pest resistance: To date, plants of the new *Hypericum* have not been observed to be resistant to pathogens and pests common to *Hypericum* plants.

Temperature tolerance: Plants of the new *Hypericum* have been observed to tolerate high temperatures about 30° C. and to be hardy to USDA Hardiness Zone 7.

It is claimed:

1. A new and distinct *Hypericum* plant named 'Allhygela' as illustrated and described.

* * * * *